United States Patent [19]

Asaka

[11] Patent Number: 5,651,974
[45] Date of Patent: Jul. 29, 1997

[54] DISINFECTANT-DETERGENT COMPOSITION

[75] Inventor: Yoshio Asaka, Yokohama, Japan

[73] Assignee: Shiseido Co., Ltd., Tokyo, Japan

[21] Appl. No.: 676,900

[22] Filed: Jul. 8, 1996

Related U.S. Application Data

[63] Continuation of Ser. No. 314,715, Sep. 29, 1994, abandoned.

[30] Foreign Application Priority Data

Sep. 30, 1993 [JP] Japan ................................. 5-268059

[51] Int. Cl.$^6$ ........................................................ A01N 25/30
[52] U.S. Cl. .................................................... 424/405
[58] Field of Search ................................................ 424/405

[56] References Cited

U.S. PATENT DOCUMENTS 4,900,544 2/1990 Ritter et al. ........................... 424/70.21
5,372,744 12/1994 Kamegai ............................... 424/70.21

OTHER PUBLICATIONS

Mori et al., *Chemical Abstracts*, vol. 117, 1990, #178090.
Sasaki et al., *Chemical Abstracts*, vol. 116, 1991, #167956.
Kobayashi, *Chemical Abstracts*, vol. 100, #161683 (1982).

*Primary Examiner*—Carlos A. Azpuru
*Attorney, Agent, or Firm*—Townsend & Banta

[57] ABSTRACT

A disinfectant-detergent composition is provided comprising amphoteric surfactant comprised of imidazolinium betaine as a main detergent, a cationic disinfectant, lower alcohol and an emollient. The disinfectant-detergent composition of the present invention has an excellent disinfecting effect, and a moderate cleansing effect without causing skin roughness, stickiness or an unfavorable reaction with a quick drying type disinfectant.

4 Claims, No Drawings

DISINFECTANT-DETERGENT COMPOSITION

CROSS REFERENCE TO A RELATED APPLICATION

This is a file wrapper continuation application of application Ser. No. 08/314,715 filed Sep. 29, 1994, now abandoned.

FIELD OF THE INVENTION

The present invention relates to a disinfectant-detergent composition and, more particularly, to an improved composition useful in hand disinfection and cleaning without causing skin roughness.

BACKGROUND OF THE INVENTION

Recently, infection in a hospital has been a very serious problem, and it is very important to prevent infection in a hospital as well as medical care of a patient. It is known that the infection in a hospital is caused by health care providers as a vector. Therefore, disinfection of a the hands of health care providers is necessary after rendering medical care to a patient.

Examples of conventional disinfectant compositions are ethanol solutions including a cationic disinfectant such as benzalkonium chloride or chlorhexidine gluconate. However, it is customary to cleanse the hands using a fatty acid soap before disinfecting the hands to improve the disinfection effect. The fatty acid soap has a strong deferring effect and a harmful influence on skin roughness. Further, the fatty acid soap is an anionic substance, so that, when the detergent is not completely removed by rinsing, a cationic disinfectant reacts with the fatty acid soap and the effect of the disinfectant is reduced. In the medical field, the reaction between anion and cation is not widely recognized and, complete rinsing of the hands is difficult. Furthermore, micro-organisms can easily contaminate rough skin on the hands and secondary infection may be caused.

As described above, a disinfectant-detergent composition which has excellent a disinfection effect without causing skin roughness and a unfavorable reaction with a quick drying type cationic disinfectant is desired by medical workers who have to disinfect their hands frequently so as to prevent the infection in a hospital.

SUMMARY OF THE INVENTION

It is an object of the present invention to eliminate the problems of the prior art and to provide a disinfectant-detergent composition which has excellent disinfection effect, moderate defatting effects and cleansing effects without causing skin roughness, stickiness or a reaction with quick drying type cationic disinfectants.

As a result of studies undertaken by the present inventors so as to achieve these goals, it has been found that a certain mixture of emollient and detergent can achieve the objectives. On the basis of these findings, the present invention has been achieved.

In the first aspect of the present invention, there is provided a disinfectant-detergent composition comprising: an amphoteric surfactant comprised of imidazolinium betaine as a main detergent, a cationic disinfectant, lower alcohol and an emollient.

The term "disinfectant-detergent composition" is used herein to encompass a disinfectant-detergent composition not only for hands and fingers but also for skin the of a patient, for a medical device and for bedclothes which can be used in the medical field, in a home and in a home for the aged.

The amphoteric surfactant comprised of imidazolinium betaine of the present invention may comprise substances represented by the following formulas 1 or 2:

FORMULA 1;

$$\begin{array}{c} N-CH_2 \\ R^1-C \overset{\|}{\underset{\diagdown}{\phantom{X}}} \quad | \\ \underset{+}{N}-CH_2 \\ / \quad \diagdown \\ (CH_2)_x \quad (CH_2)_x OH \\ | \\ COO^- \end{array}$$

FORMULA 2;

$$R^1-\overset{O}{\overset{\|}{C}}-NHCH_2CH_2N\diagup^{(CH_2)_xOH}_{\diagdown (CH_2)_xOH}$$

wherein $R^1$ represents a straight or branched alkyl group or alkenyl group having carbon atoms of 7–21. x represents an integer 1 or 2.

The amphoteric surfactant may comprise OBAZOLIN 662N (trade name of TOHO KAGAKU CORP.), ANON GLM (trade name of NIHON YUSHI COPR.) and MILANOL DM (trade name of MILANOL CORP.).

The imidazolinium betaine has a moderate cleaning and defatting effects. The mount of surfactant is from 1 to 40 w/v % and preferably from 5 to 20 w/v % in cleaning effect and easy rinsing. Other amphoteric surfactants generally have strong stimulant actions on the skin or eyes, or too strong a defatting effect. Although the imidazolinium betaine has weak antibacterial action, the action can be made up by other antibacterial substances.

The cationic disinfectant of the present invention may comprise benzalkonium chloride having carbon atoms from 8 to 18, benzethonium chloride, chlorhexidine gluconate, alkyl isoquinolinium bromide, alkyl trimethylammonium chloride having carbon atoms from 8 to 24, and N-cocoyl-L-arginine ethyl ester-DL-pyrrolidone carbonate (CAB) represented by the formula 3:

$$\begin{array}{c} R^2CO-NHCHCOOC_2H_5 \quad NH \quad\quad CH_2-CH_2 \\ | \quad\quad\quad\quad\quad\quad\quad \| \quad\quad / \quad\quad\quad \diagdown \\ CH_2CH_2CH_2NHC.O=C \quad\quad\quad\quad CH-COOH \\ | \quad\quad\quad\quad\quad \diagdown \quad\quad\quad\quad / \\ NH_2 \quad\quad\quad\quad\quad\quad NH \end{array}$$

wherein $R^2CO$- is a residue of coconut fatty acid.

The cationic disinfectant comprises an ordinal content of disinfectant such as 0.01–4 w/v % and, more preferably 0.1–2 w/v % in accordance with solubility of the disinfectant.

The lower alcohol of the present invention may preferably comprise ethanol or isopropyl alcohol. The amount of ethyl alcohol is preferably in the range of 25–80 v/v % in accordance with disinfection effect. However, the amount of ethanol may be enough in the range of 10–25 v/v % of ethanol solution. Further, it is particularly effective to add 1.0–10.0 v/v % of isopropyl alcohol to the composition disinfection effect.

3

The emollient of the present invention may preferably comprise glycerin, erythritol, polyethylene glycol, propylene glycol, butylene glycol, pentylene glycol, hexylene glycol, dipropylene glycol, sorbitol and maltitol in view of preventing stickiness and skin roughness caused by lowel alcohol. Particularly preferred emollient is glycerin. The emollients of the present invention can be easily and completely dissolved in a ethanol solution and, muddiness, precipitation and separation can not be observed. Further, the emollients do not influence the disinfection effect of the cationic disinfectants, but rather maintain the disinfectant effect on the applied skin.

The amount of emollient may be in the range of 0.1–15.0 w/v % and, more preferably in the range of 1–7 w/v %. In the case where the content of the emollient is less than 0.1 wt %, it may not be enough to obtain to prevent the effect of skin roughness. Also, in the case where the content of the emollient is over 15.0 w/w %, it may not be possible to prevent stickiness.

pH of the composition is usually 7.0±2 and more preferably from 7 to 9. In the case where the composition is used in fields other than hand disinfection, pH of the composition may be adjusted at a rather high pH. pH controllers, in this case, comprise ordinal alkaline substances. The examples are alkaline metal hydride such as sodium hydride and potassium hydride; and alkaline metal carbonate such as sodium carbonate, potassium carbonate, sodium bicarbonate and potassium bicarbonate.

The compositions of the present invention may additionally comprise other components which are well known to those skilled in the art for examples of nonionic surfactants which can be used as sub-detergents and urea which can be used as a skin protector.

EXAMPLES

A preferred embodiment of the present invention will be explained hereinunder. The content is expressed by weight %.

EXAMPLES 1 TO 6, COMPARISON 1 AND 2

1–5% of glycerin was uniformly dissolved in 20% ethanol solution including 5–15% of an amphoteric surfactant comprised of imidazolinium betaine (OBAZOLIN 662N) and 0.5% of benzalkonium chloride. The contents of these ingredients was changed according to each sample and the efficacy of the compositions were measured in user tests. The tested items were, preventing effect of skin roughness, stickiness after drying and emollient effect after drying. The users consisted of 10 persons and the results were given as an average of the index the users evaluated.

EVALUTION STANDARD

3: excellent

2: good

1: average

0: not good

Furthermore, a disinfection effect test was conducted according to the following method.

Staphylococcus aureus FDA 209P was cultured in a liquid bouillon culture medium for 20 hours at 37° C., The medium was diluted 200 times by adding sterilized water. 0.1 ml of the diluted medium (including about $10^6$ cfu of the staphylococcus) was added in 10 ml of the disinfectant-detergent composition and stirred to be uniform. After 30 sec., 0.1 ml of the composition was collected by a pipette, and measured plate count using SCDLP agar culture medium by Smear method. The killing ratio was calculated from the plate count/$10^4$ cfu(100% recovery).

The results are given below.

TABLE 1A

|  | COMPARISON | | EXAMPLE | | | | | |
|---|---|---|---|---|---|---|---|---|
|  | 1 | 2 | 1 | 2 | 3 | 4 | 5 | 6 |
| Imidazolinium betaine | — | 10.0 | 5.0 | 5.0 | 10.0 | 10.0 | 15.0 | 15.0 |
| Cocoylamide propyl betaine | 10.0 | — | — | — | — | — | — | — |
| Ethanol | 20.0 | — | 20.0 | 20.0 | 20.0 | 20.0 | 20.0 | 20.0 |
| Benzalkonium chloride | 0.5 | 0.5 | 0.5 | 0.5 | 0.5 | 0.5 | 0.5 | 0.5 |
| Glycerin | 5.0 | 5.0 | 1.0 | 5.0 | 1.0 | 5.0 | 1.0 | 5.0 |
| Purified water | 74.5 | 84.5 | 73.5 | 69.5 | 68.5 | 64.5 | 63.5 | 59.5 |
| Killing ratio (30 sec.) | 90%< | 99%< | 90%< | 90%< | 90%< | 90%< | 99%< | 99%< |
| Stickiness | 1.0 | 0.8 | 1.8 | 1.3 | 1.6 | 1.0 | 1.2 | 0.9 |
| Emollient effect | 1.4 | 1.9 | 0.8 | 1.3 | 1.5 | 1.8 | 1.7 | 2.4 |
| Preventing effect on skin roughness | 0.2 | 2.3 | 1.1 | 1.6 | 1.4 | 2.3 | 1.9 | 2.3 |

EXAMPLE 7

10.0% of imidazolinium betaine (Sold under the trade name ANON GLM) and 0.25% of chlorhexidine gluconate were dissolved in 15%-ethanol solution. 1.0 w/v % of sorbitol and 4 w/v % of glycerin as emollients, and 0.02 w/v % of CAE as a disinfectant were added in the composition. Disinfection effect and cleansing effect were tested with respect to the obtained composition. The disinfection effect was tested using the grove juice method.

The test was conducted according to the following method.

Staphylococcus aureus FDA 209P was cultured in a liquid bouillon culture medium for 20 hours at 37° C. The medium was diluted 2000 times by adding sterilized saline. 1 ml of the diluted medium (including about $10^6$ cfu of the staphylococcus) was applied on both hands and rubbed and dried. The number of viable staphylococcus aureus cells is about $5\times10^5$ cfu in each hand. After drying for 10 min., 3 ml of the disinfectant-detergent composition was applied on the hand and rubbed. After 30 sec., the hand was rinsed with water for 30 sec., swished water off and the measured viable cells on the right hand by grove juice method. 50 ml of LP-dilution solution, which can deactivate the chlorhexidine gluconate, was used for collecting the micro-organisms, and the obtained micro-organisms were confirmed using SCDLP medium. The obtained micro-organisms were divided into the staphylococcus and others according to shapes, colors, and growth, differential black colonies and color changes of Vorgel-Johnson medium. A blank test was conducted according to the same way but using 50 ml of sterilized water instead of the disinfectant-detergent composition.

The results are given in Table 2. In Table 2, "<5" means less than 5 cfu/ml (=no staphylococcus can be observed).

TABLE 3

| PANEL | A | B | C | D | E | F | G | H | I | J |
|-------|---|---|---|---|---|---|---|---|---|---|
| SCORE | 2 | 2 | 1 | 1 | 2 | 2 | 1 | 3 | 2 | 2 |

As explained above, the disinfectant-detergent composition of the present invention has excellent disinfection effect and moderate cleaning effect without causing skin

TABLE 2

| PANEL | A | B | C | D | E | F | G | H | I | J |
|-------|---|---|---|---|---|---|---|---|---|---|
| Blank test: ($\times 10^5$) | 5.2 | 4.3 | 3.9 | 4.4 | 5.4 | 5.1 | 5.2 | 4.5 | 4.7 | 4.2 |
| Plate counting after the treatment | <5 | <5 | <5 | <5 | <5 | <5 | <5 | <5 | <5 | <5 |
| Stickiness after disinfection | none | none | none | none | none | none | none | none | none | none |

EXAMPLE 8

8 w/v % of imidazolinium betaine (Sold under the trade name MILANOL DM) and 0.3% of chlorhexidine gluconate were dissolved in 15%-ethanol solution. 4.0 w/v % of glycerin as an emollient and 2% of isopropyl alcohol were added in the composition.

The composition so obtained was tested as to preventing the effect of roughness skin under repeated use.

The test was conducted according to the following method.

3 ml of the prepared disinfectant-detergent composition was applied on the hands, rubbed and washed. After 30 sec., the hand was rinsed by water for 30 sec., the water was swished off and dried with a towel. The same procedure was repeated for 10 times at intervals of 15 minutes. 10 persons conducted the test and the test was repeated for 5 days. The skin roughness was evaluated independently. The results of each persons are given in TABLE 3. The evaluating method is same as Example 1.

roughness, stickiness or a reaction with quick drying type cationic disinfectant.

What is claimed is:

1. A method of disinfecting hands comprising applying to the hands a disinfectant-detergent composition comprising amphoteric surfactant comprised of imidazolinium betaine as a main detergent, a cationic disinfectant, lower alcohol and an emollient.

2. The method of disinfecting hands according to claim 1, wherein the lower alcohol is ethanol and/or isopropyl alcohol.

3. The method of disinfecting hands according to claim 1 wherein the lower alcohol comprises equal or less than 25 w/v % of the composition.

4. The method of disinfecting hands according to claim 1, wherein the emollient is selected from glycerin, erythritol, polyethylene glycol, propylene glycol, butylene glycol, pentylene glycol, hexylene glycol, dipropylene glycol, sorbitol and maltitol.

* * * * *